United States Patent [19]

Mitchell

[11] 4,281,145
[45] Jul. 28, 1981

[54] PROCESS FOR PRODUCING ALKOXYLATED SILANES

[75] Inventor: Tyrone D. Mitchell, Albany, N.Y.

[73] Assignee: General Electric Company, Waterford, N.Y.

[21] Appl. No.: 136,640

[22] Filed: Apr. 2, 1980

[51] Int. Cl.³ .............................. C07F 7/18; C07F 7/04
[52] U.S. Cl. .............................. 556/440; 260/410.9 R; 556/418
[58] Field of Search .............................. 556/440, 418; 260/410.9 R

[56] References Cited

U.S. PATENT DOCUMENTS

| | | | |
|---|---|---|---|
| 3,427,337 | 2/1969 | Miller et al. | 556/440 |
| 3,759,968 | 9/1973 | Berger et al. | 556/440 |
| 3,773,817 | 11/1973 | Berger et al. | 556/440 X |

FOREIGN PATENT DOCUMENTS 1337516  8/1963  France .
1099619  1/1968  United Kingdom .

*Primary Examiner*—Paul F. Shaver
*Attorney, Agent, or Firm*—E. Philip Koltos; J. L. Young; E. Philip Schlamp

[57] ABSTRACT

A process for preparing silyl maleates, fumarates, succinates and phthalates comprising reacting an olefinic containing maleates, fumarates, succinates or phthalates with hydrogenotrichlorosilane in the presence of the platinum catalyst and then reacting the product thereof with methanol wherein the methanol is added slowly over a period of at least 6 hours to the intermediate product such that it is introduced beneath and into the liquid layer of intermediate product where most of the HCl that is formed by the reaction is removed by azeotroping it out with the methanol and water along with the HCl dissolved therein and removing the azeotrope as it being formed.

63 Claims, No Drawings

PROCESS FOR PRODUCING ALKOXYLATED SILANES

BACKGROUND OF THE INVENTION

The present invention relates to the production of the silyl maleates and more particularly the present invention relates to a novel process for maximizing the yield of the production of silyl maleates, fumarates, succinates and phthalates.

Silyl maleates are well-known, for instance, see the disclosure of U.S. Pat. No. 3,759,968 which is hereby incorporated by reference, with respect to silyl maleates also seen in the disclosure of French Pat. No. 1,337,516, U.S. Pat. No. 3,179,612 and British Pat. No. 1,099,619. When such silyl maleates were first developed, they were disclosed as being utilized as self-bonding additives for heat curable silicone rubber compositions. In a later patent application which is still pending, silyl maleates, fumarates, and succinates are disclosed as self-bonding additives for incorporation into one component room temperature vulcanizable silicone rubber compositions. Silyl phthalates were not disclosed in that patent application, which is Ser. No. 52,042, Smith et al, entitled "Shelf-Stable One Part Room Temperature Vulcanizable Silicone Rubber Compositions" filed Feb. 28, 1979. Although silyl phthalates were not disclosed in that patent application for use as self-bonding additives, they do have some utility as self-bonding additives for heat vulcanizable silicone rubber compositions. However, there was some difficulty with the process for the production of such silyl maleates, fumarates, succinates and phthalates (hereinafter, while reference is made to silyl maleates, it is understood that the same process conditions apply to the fumarates, succinates, and phthalates).

Accordingly, the processes that were disclosed in, for instance, U.S. Pat. No. 3,773,817 and related patents on the production of silyl maleates, fumarates, and other related compounds were not altogether advantageous. The difficulties of such processes will be disclosed below but to state matters simply the overall yield from such a process did not exceed 60 percent most of the time and many times the overall yield was considerably lower. There were two alternate processes of the prior art such as disclosed in the foregoing Berger et. al. U.S. Pat. No. 3,773,817 which was disclosed for the production of silyl maleates. One process was the taking of trimethoxyhydrogenosilane and reacting with the olefinic maleate. The disadvantage of this process was that hydrogenotrimethoxysilane is very hard to handle since it is dangerous material that can cause eye damage. In addition, the reaction is exothermic and difficult to control. In another aspect, the trimethoxyhydrogenosilane is the product of alkoxylating hydrogenotrichlorosilane which in itself is a difficult process for the reason that will be set forth below. Accordingly, a more acceptable process from the material handling point of view to react the olefin maleate with trichlorosilane in the presence of a platinum catalyst to produce trichlorosilylpropylmaleate. The resulting maleate was alkoxylated by reacting the trichlorosilylmaleate with methanol in the presence of an aromatic solvent at the temperature of 25° to 70° C. as disclosed in the foregoing U.S. Pat. No. 3,773,817.

The difficulty with such a reaction was that the methanol reacts with hydrogen chloride that is formed to produce methyl chloride and water. This is a competing reaction which tends to predominate and accordingly, the desired yield of a methoxylated product would be quite small. An undesirably side reaction would be that if the methyloxylation of the trichlorosilylpropylmealeates continues the alcohol and would react with a methoxysilylpropyl maleates in the presence of hydrogen chloride to cleave the trimethoxysilylpropyl ester group and yield a methoxy maleate ester. Both of these reactions as can be appreciated would give the desired yield of a methoxylated silylpropylmaleate compound. Accordingly, this methoxylation was hard to control and high yields were difficult to obtain utilizing the technique set forth in U.S. Pat. No. 3,773,817 and elsewhere.

Another alternative process was to use trimethylorthoformate to carry out methoxylation of bis-(trichlorosilylpropyl) maleate. However, the cost of this process is prohibitive such as to make it disadvantageous to use even though the proces operates properly and results in a high yield of product. It takes 6 moles of the trimethylorthoformate for one mole of a maleate to produce the desired methoxylated product. Accordingly, in spite of the fact that this process with trimethylorthoformate is desirable in that it results in a high yield of product with a minimum of side reaction, nevertheless, it is prohibitively expensive. Accordingly, it was highly desirable to find an inexpensive route for the production of methoxylated silylpropylmaleates fumarates, succinates, and phthalates. This was true whether there was one methoxy per silicon atoms in the maleate or three methoxy groups per silicone atom in the maleate, fumarate, succinate, phthalate.

Accordingly, it is one object of the present invention to provide an economical process for producing alkoxylated silyl maleates, fumarates, succinates, and phthalates.

It is an additional object of the present invention to provide an efficient and economic process for the production of alkoxylated silyl maleates, fumarates, succinates, and phthalates in over 75% yield.

It is an additional object of the present invention to provide a safe process for the production of alkoxylated silyl maleates, fumarates, succinates, and phthalates which does not result in the handling of hazardous or dangerous materials.

It is still an additional object of the present invention to provide a process for the production of alkoxylated silylmaleates, fumarates, succinates, and phthalates.

The process is carried out such that the entire addition reaction as well as the alkoxylation reaction takes place in one reaction chamber which results in an economical utilization of process conditions and process materials. These and other objects of the present invention are accomplished by means of a disclosure set forth herein and below.

SUMMARY OF THE INVENTION

In accordance with the above objects there is provided by the present invention a process for producing silyl maleates comprising (a) reacting a maleate of the formula,

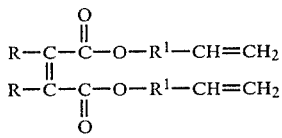
(1)

with

(2)

in the presence of a platinum catalyst and (b) then mixing and reacting the intermediate product with an aliphatic alcohol of the formula $R^2OH$ where said intermediate product is present in an organic solvent and where said aliphatic alcohol is added to said intermediate product beneath and into the layer of said intermediate product and where said intermediate product is maintained at or near the reflux temperature of said organic solvent during said addition to produce in at least 75% yield a silyl maleate of the formula,

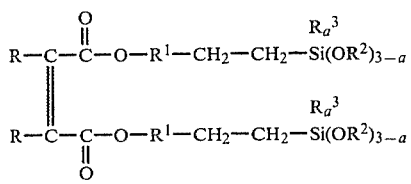
(3)

where $R^2$ and $R^3$ are monovalent hydrocarbon radicals of 1 to 8 carbon atoms, R is selected from hydrogen and monovalent hydrocarbon radicals of 1 to 8 carbon atoms, a varies from 0 to 2, X is halogen and $R^1$ is a divalent hydrocarbon radical of 0 to 8 carbon atoms.

A similar process conditions apply for the production of the silyl maleates, silyl fumerates, silyl succinates, and silyl phthalates as will be disclosed below. An important aspect of the process of the instant case is to remove the hydrogen chloride that is formed during the reaction as soon or in close proximity to when it is formed by refluxing it out as a gas and by trapping it in an azeotrope of methanol, organic solvent and water where the methanol, water and dissolved hydrogenchloride is continually removed as the lower layer from a trap which collects the condensed vapors from the reflux. The upper layer is returned to the vessel. This removal of the HCl prevents it from building up and reacting it with methanol to produce methyl chloride and water. Another important aspect of the methoxylation process of the instant case is that at the point where the reaction is close to being completed; that is, where 10,000 parts per million or less of silyl chloride bonds (Si—Cl) are present there is added sufficient methanol and tertiary amine on an alkali metal alkoxide to terminate the reaction.

The methanol will react with Si—Cl bonds remaining in the reactant maleate or the compound to produce the desired methoxyated product where the tertiary amine in the reaction mixture will react with HCl that is given up to tie it up so that the HCl will not catalyze a cleavage reaction as was discussed above. Utilizing this procedure, it is possible to obtain as much as 75 percent yield and more likely, at least 80% of the desired alkoxylated or methoxylated silyl maleate, fumarate, succinate, or phthalate.

DESCRIPTION OF THE PREFERRED EMBODIMENT

A similar manner as above there is encompassed within the instant invention process for the production of silyl fumarates comprising reacting a fumarate of the formula,

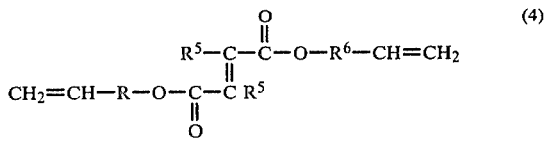
(4)

with (5) 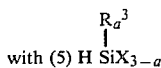

in the presence of a platinum catalyst and (b) then reacting the intermediate product with an aliphatic alcohol of the formula $R_0^2H$ where said intermediate product is present in an organic solvent and where said aliphatic alcohol is added to said intermediate product slowly over a period of at least six hours wherein said intermediate product is maintained at the reflux temperature of said organic solvent during said addition of said alcohol to produce in at least 75% a silyl fumarate of the formula,

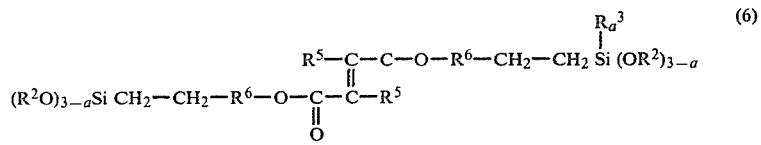
(6)

where $R^2$ and $R^3$ are monovalent hydrocarbon radicals of 1 to 8 carbon atoms, $R^5$ is selected from hydrogen and monovalent hydrocarbon radicals of 1 to 8 carbon atoms, a varies from 0 to 2, X is halogen and preferably chlorine, and $R^6$ is a divalent hydrogen radical of 0 to 8 carbon atoms.

In yet another embodiment of the instant invention is provided by the instant invention a process for producing silyl succinates comprising (a) reacting a silyl succinate of the formula,

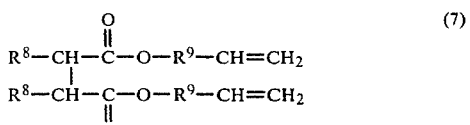
(7)

(8)

in the presence of a platinum catalyst and (b) then reacting the intermediate silyl product with an aliphatic alcohol of the formula $R^2OH$ where said intermediate product is present in an organic solvent and where said aliphatic is added to said intermediate product slowly over a period of at least six hours wherein said intermediate product is maintained at the reflux temperature of said organic solvent during said addition to produce in at least 75% yield or silyl succinate of the formula,

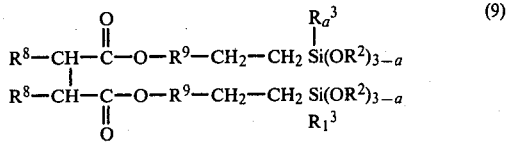

where $R^2$ and $R^3$ are monovalent hydrocarbon radicals of 1 to 8 carbon atoms, $R^8$ is selected from hydrogen and monovalent hydrocarbon radicals of 1 to 8 carbon atoms, a varies from 0 to 2, X is halogen and preferably chlorine, and $R^9$ is a divalent hydrocarbon radical of 0 to 8 carbon atoms.

Still, another embodiment of the present invention there is provided a process for producing silyl phthalates comprising (a) reacting a phthalate of the formula,

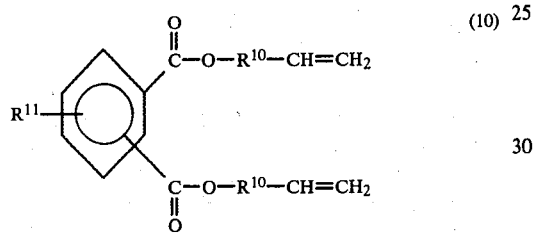

with

in the presence of a platinum catalyst and (b) then reacting the intermediate silyl product with an aliphatic alcohol of the formula $R^2OH$ where said intermediate product is present in an organic solvent and where said aliphatic alcohol is added to said intermediate product slowly over a period of at least six hours wherein said intermediate product is maintained at the reflux temperature of said organic solvent during said addition to produce in at least 75% yield silyl phthalate of the formula,

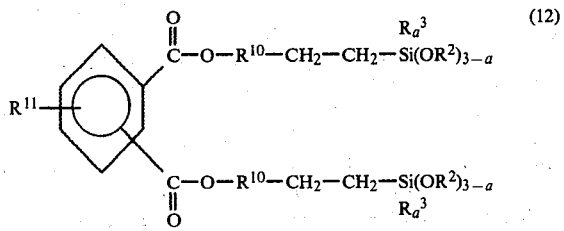

where $R^2$ and $R^3$ are monovalent hydrocarbon radicals of 1 to 8 carbon atoms, $R^{11}$ is selected from hydrocarbon halogen, nitro and hydrogen, a varies from 0 to 2, X is halogen, and preferably chlorine and $R^{10}$ is a divalent hydrocarbon radical of 0 to 8 carbon atoms. The silyl maleate intermediate product identified in the above reaction has the following formula,

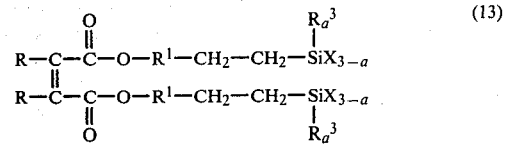

The silyl fumarate intermediate product has the formula,

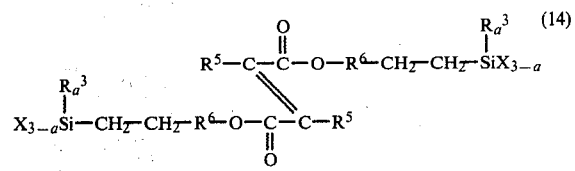

The silyl succinate intermediate product has the following formula,

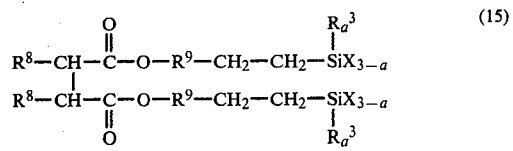

The silyl phthalate intermediate product has the following formula,

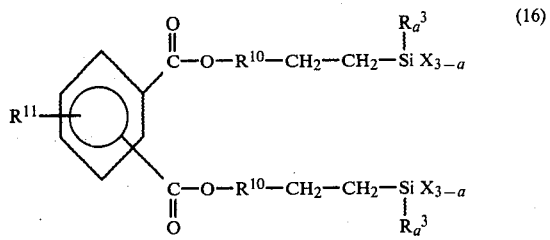

In the above formulas, $R^2$ and $R^3$ can be any monovalent hydrocarbon radical of 1 to 8 carbon atoms. Preferably such radicals are selected from alkyl radicals of 1 to 8 carbon atoms such as methyl, ethyl, propyl, etc.; cycloalkyl radical such as cyclo hexyl, cycloheptyl; mononuclear aryl radicals such as phenyl, methylphenyl, ethylphenyl, etc.; haloalkyl radicals such as 3,3,3-trifluoropropyl, etc.; and alkenyl radicals such as vinyl, allyl, etc. More preferably $R^2$ and $R^3$ are selected from alkyl radicals of 1 to 8 carbon atoms and phenyl radicals. The radicals R and $R^8$, $R^5$ and can any of the radicals disclosed above for $R^2$ and $R^3$ and in addition can be hydrogen. More preferably the R, $R^5$ and $R^8$ radicals are selected from alkyl radicals of 1 to 8 carbon atoms and phenyl. The $R^{11}$ radical can be any hydrogen radical preferably chlorine, nitro or hydrogen, most preferably it is hydrogen or an alkyl radical of 1 to 8 carbon atoms. The radicals $R^1$, $R^6$, $R^9$ and $R^{10}$ are any divalent hydrocarbon radicals of 0 to 8 carbon atoms and more preferably are alkylene and arylene radicals of 1 to 8 carbon atoms. In the above formulas, a varies from 0 to 2 and is most preferably 0.

Accordingly, in the most preferred compounds of the instant invention there are three alkoxy radicals per silicone atoms. It should be understood there can be as little as one alkoxy radical per silicone atom in the compounds in the instant case. In the most preferred case there are three alkoxy radicals per silicone atoms since that gives the products with the best self-bonding properties or the best self-bonding properties to room temperture vulcanizable silicone rubber compositions. In the description below, the description refers specifically to the production of the silyl maleates of Formula (3). However, it should be understood that process conditions and other process limitations defined for the silyl maleates to be disclosed below applies to the production also of the other silyl compounds such as silyl fumarates, silyl succinates, and silyl phthalates. In the first reaction of the instant process when X is preferably chlorine, trichlorosilane is reacted with the olefinic maleate of Formula (1) in the presence of a platinum catalyst. Preferably the reaction is carried out in the presence of an organic solvent which results in more intimate contacting of the reactants. Any organic solvent may be utilized and preferably there are utilized aliphatic hydrocarbon solvents, aromatic hydrocarbon solvents such as heptane, pentane, hexane, cyclohexane, xylene, toluene. The most preferred solvents being toluene or hexane. Examples of other organic solvents that may be utilized are as follows: ethylether, dimethoxyethylether, methylene chloride, carbontetrachloride, chloroform, dioxane, pentane, hexane, heptane, octane, cyclohexane, benzene, toluene, xylene chlorobenzene, dichlorobenzene, trichloroethane. etc.

When reference is made to an organic solvent, it is understood that any of the above solvents may be utilized in the process of the instant case. The platinum catalyst that may be utilized may be solid platinum disposited in charcoal or solid platinum deposited on gamma alumina. Most preferably the platinum is a solubilized platinum catalyst such as that disclosed in Lamoreaux U.S. Pat. No. 3,220,972.

The reaction temperature can be anywhere from room temperature to 150° C. and preferably the reaction is carried out at elevated temperature of anywhere from 50° to 100° C. If the temperature is raised too high, the reaction is difficult to control and if it is too low the reaction does not go at a sufficient rate. It should be pointed out that the pressure can be utilized at this part of the process but it is not necessary. Accordingly, even though pressure could be utilized in the first step of the process, it is preferably not utilized since it does not serve a real useful purpose. It does not offer any additional advantages and necessitates the use of pressure equipment. It should be noted that the trichlorosilane is preferably utilized at a concentration of 10 to 30 percent in excess since that helps to push the reaction to completion as far as the maleate of Formula (1) is concerned and results in the highest yield of desired product of silyl maleate intermediate product of Formula (13). In this hydrosilation reaction, $SiCl_4$ is formed as a by-product. The product of $SiCl_4$ with methanol is very toxic and can cause blindess. Accordingly, before it is desired to carry on the alkoxylation of the chlorine groups in the silyl maleate it is necessary to remove all of this $SiCl_4$ foreign by-product. To do this, an organic solvent is added in additional amounts such as 25 to 300 percent by volume of the reaction mixture and $SiCl_4$ is distilled out or refluxed out along with the solvent. The preferred solvents for doing this is toluene or xylene. Accordingly, by adding toluene and heating the mixing in excess of 100° C. there is formed an azeotrope of toluene and $SiCl_4$ from the silyl maleate intermediate product of formula (13). It should be noted that the azeotrope is removed by refluxing the reaction mixture in which the additional solvent is added. It should be noted that the additional solvent does not have to be added if there is sufficient solvent added in the initial part of the reaction. However, if such solvent has not been added or if an insufficient amount of solvent has been added to the reaction mixture then additional amounts of solvents can be added as pointed out previously and the $SiCl_4$ is refluxed out along with the solvent. Preferably a solvent is added to form an azeotrope with the $SiCl_4$ so that azeotrope can be refluxed out off the reaction mixture to get rid of the $SiCl_4$. A preferred solvent for this purpose is toluene; however, any other solvent that forms an azeotrope with $SiCl_4$ may be utilized. Reflux temperature of this azeotrope is above 100° C. and is in the range of 100° to 130° C. The refluxing is preferably at atmospheric pressure to remove the $SiCl_4$ through this procedure. This refluxing out of this $SiCl_4$ usually takes place over a period of time from anywhere from 1 to 6 hours.

The first part of this process, the hydrosilation reaction or addition of the trichlorosilane to the silyl maleate of Formula (1) takes place in anywhere from 1 to 3 hours. After this reaction and removal of the $SiCl_4$ is completed there is left in the reaction mixture the intermediate of Formula (13). It should be pointed out that the whole process may be carried in a single reaction vessel and there is left in the single vessel, the silyl maleate of Formula (13) and the organic solvent. To this mixture is added an alcohol and most preferably an aliphatic alcohol of 1 to 3 carbon atoms and most preferably the alcohol is methanol. To 50% to 300% by weight of excess methanol is added to a reaction mixture so as to be sure to drive the methoxylation or alkoxylation reaction to completion. It should be noted here that the aliphatic alcohol of 1 to 8 carbon atoms and most preferably methanol is added to the liquid layer of solvent and silylmaleate intermediate product of formula (13) so that it will not come in contact with the hydrogen chloride by-product to yield methyl chloride and water; a side reaction which if it predominates will considerably reduce the yield of the desired product of Formula (3).

Another and critical part of the instant invention is that the methanol or aliphatic alcohol of 1 to 8 carbon atoms is added slowly to the reaction mixture in the pot. Normally the total amount of the aliphatic alcohol will be added over a period of at least 6 hours and more preferably will be added over a period of from 6 to 36 hours and most preferably from 10 to 24 hours. The aliphatic alcohol must be added slowly over this period of time since if it is added too fast it will tend to produce large amounts of HCl which cannot be removed fast enough and which large amounts of HCl will react with large amounts of aliphatic alcohol present to produce methyl chloride and water by means of the competing reaction. Accordingly, to keep this side reaction a minimum it is necessary to add the aliphatic alcohol slowly to the reaction mixture, specifically to the organic solvent and silyl maleate intermediate product of Formula (13) slowly over a period of time as stated previously of at least 6 hours and more preferably from 6 to 36 hours so that a maximum amount of the desired silyl maleate product in Formula (3) can be obtained. Another part of the process that should be carried to keep the reaction of methanol with hydrogen chloride to a minimum so that the yield of silyl maleate intermediate product of Formula (13) is maximized is that organic solvent is heated to a reflux temperature of the mixture so as to continually distilled overhead an azeotrope of the excess aliphatic alcohol and the organic solvent in which there is dissolved therein some of the hydrogen chloride that is given off by the alkoxylation reaction. This azeotrope layer after it forms in the reflux trap must be removed continually so as to keep the hydrogen chloride and alcohol from building up in the reaction vessel. It should be noted that a minimum of alcohol is needed. The alcohol is present at 50 to 300 mole percent in excess just as there was from 10 to 30 mole percent in excess of trichlorosilane in the first reaction. In the second reaction there must be present at least 50 to 300 mole percent of aliphatic alcohol so as to drive the reaction to completion. This is done by the aliphatic alcohol forming an azeotrope with the hydrogen chloride or hydrohalogen gas to produce a constant boiling mixture with the solvent which is then removed in an azeotrope. It should be noted that the azeotrope does not appear usually until 40% of the total amount of methanol that will be added has been fed to the reaction pot. However, once the azeotrope layers appears in the reflux tray, the lower azeotrope is continually removed so as to get rid of the HCl gas so as to keep the side reaction of the aliphatic alcohol with the hydrogen chloride to a minimum, to remove the hydrogen chloride gas away from the reaction pot so that it will not remain in the reaction pot and react with the aliphatic alcohol.

The organic solvent in this last reaction is preferably toluene but it can be any organic solvent disclosed above and is preferably an aliphatic hydrocarbon organic solvent and an aromatic hydrocarbon solvent. It is most preferably hexane or toluene. During the total reaction period in the second reaction, the reaction mixture of the silyl maleate of Formula (13) along with the organic solvent and the added alcohol which is preferably methanol is maintained at the reflux temperature of the reaction mixture. Toluene is an organic solvent which can be utilized throughout the entire process. Then the reaction mixture is maintain at a reflux temperature above 100° C. and more preferably at a temperature of above 100° and up to 130° C. In this second reaction, the process is carried out at atmospheric pressure since hydrogen chloride gas and the azeotrope has to be removed by refluxing. It should be noted that it is necessary to use an organic solvent in this second reaction. It should be noted that in the solution of this organic solvent in the second reaction, it is necessary, if it is not toluene, that the organic solvent that will be utilized will form an azeotrope with the alcohol and preferably methanol. That is so that an azeotrope layer can be collected in a reflux trap and separated out from the reaction chamber so as to continually remove the hydrogen chloride gas that is formed during the alkoxylation reaction.

The reaction period for this second reaction is basically the time of addition of the methanol is accordingly at least six hours long and up to 36 hours and is more preferably from 10 to 24 hours long. During the reaction the silyl maleate intermediate of Formula 13, is continually analyzed to determine how much of this intermediate is still left in the reaction pot and specifically how much silicon chloride bonds are left in the reaction pot. Although the analysis is carried in terms of hydrogen chloride it is really a measure of the amount of Si—Cl there is still present in the reaction vessel as the silyl maleate of Formula (B). When it is determined that there is 10,000 parts per million of SiCl or less, the reaction first is cooled to room temperature and there is added sufficient tertiary amine on an alkali metal alkoxide along with methanol in the reaction pot so as to completely alkoxylate the SiCl remaining in the reaction pot and to tie up all of the hydrogen chloride that is formed as a result of this reaction with tertiary amine.

The tertiary amines that can be used are of the formula $R_3{}^{15}N$ where $R^{15}$ is alkyl radical or cycloalkyl radical or an aryl radical of 1 to 8 carbon atoms, most preferably $R^{15}$ is an alkyl radical of 1 to 15 carbon atoms and is most preferably triethylamine. The reason for the addition of the triethylamine with the stoichiometric amount of aliphatic alcohol which materials are added at a slight access to the stoichiometric amount necessary is to completely alkoxylate the silyl maleate to product of Formula (3) and to use up all the HCl that is given off as the result of the alkoxylation. The tertiary amine comlexes with the hydrogen chloride as the result of the following reactions that take place as one approaches the complete alkoxylation of the silyl maleate intermediate product of Formula (13) in the reaction vessel.

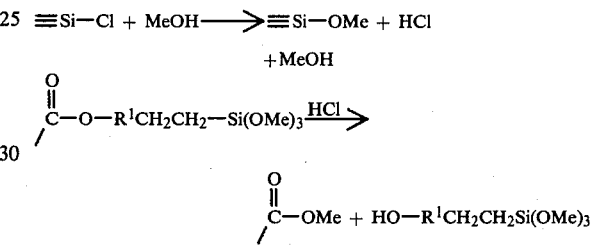

The reactions above show as one approaches the complete alkoxylation of a silyl maleate intermediate product of Formula (13) the methanol, in the the presence of HCl, will react with the trimethoxysilylpropoxy group, cleave the group and replace it with a methoxy group. Accordingly, the addition of a tertiary amine on alkali metal salt of an aliphatic alcohol of 1-8 carbon atoms along with the stoichiometric amount of methanol is to keep this cleavage reaction to a minimum. It is preferably to keep the cost of the process as low as possible and that the tertiary amine or alkali metal alkoxide along with a stoichiometric amount of aliphatic alcohol be added to the reaction mixture after it has cooled to room temperature when there is less than 2000 parts per million of SiCl remaining, when measured as HCl in the reaction chamber. It should be noted that the entire alkoxylation reaction could be carried out by the use a tertiary amine as a hydrogen chloride accepter which would do away with the parts of the process which require removal of HCl by the refluxing of the azeotrope. However, the uses of large amount of tertiary amine in the process of the instant case result in the process in becoming very expensive. Accordingly, the tertiary amine is added at the terminal part of the entire reaction so as to keep the cost of the process to a minimum.

Sufficient tertiary amine is added along with the aliphatic alcohol and more specifically methanol and triethylamine until in the reaction mixture there is left less than 50 parts million of ≡SiCl. When this value has been reached than for all practical purposes most of the ≡Si—Cl has been converted from the silyl maleate intermediate product of Formula (13) to the desired product of Formula (3). Accordingly, then the organic solvent is distilled off by vacuum distillation and the final product is filtered so as to removed the tertiary amine chloride salts by filtration to yield the deisred product in at least 75% yield. This 75% yield is an overall yield. The yield in accordance with the instant invention in the first part of the process is 88%, the yield in the second part of the process is at least 85% and the overall yield of the two processes or of the two reaction is at least 75% and more preferably at least 80%. In order that the instant invention be applied to produce silyl fumarate of the formula as disclosed above, silyl succinates and silyl phthalates as disclosed above, the same process conditions as was given with respect to the production of the silyl maleates of Formula (3) are utilized. The only changes are those carried by the different materials. Accordingly, the reflux temperature will be different for the production of these other compounds and also the reaction temperature will vary and the reflux temperatures will vary as solvents other than toluene are utilized. It should be noted that the reflux temperature of the particular reaction will vary depending on what organic solvent is used and depending on what the reactant or intermediate product in the reaction is. Also, the amount of azeotrope to be removed during the process may vary depending on the alcohol used. It is expected that the amount of azeotrope seen will be directly proportioned to the reactivity of the alcohol with HCl. That is, the greater the tendency of the alcohol to form water and alkyl halide the more azeotrope will be observed. In other respects, the process conditions should stay the same. The examples given below are given for the purpose of illustrating the present invention. They are not given for any purpose of setting limits and boundaries to the instant invention. All parts in the examples are by weight.

EXAMPLES 1-17

To a 5,000 mL, three-necked flask was attached a thermometer, a mechanical stirrer, a 2,000 mL dropping funnel and a Dean-Stark azeotrope trap with a water-cooled condenser attached. To the flask was added 880 parts (2 moles) of bis(3-trichlorosilylpropyl)maleate and 1320 parts (1524 mL) of anhydrous toluene. To the dropping funnel was added 1029 parts (32.2 moles) of anhydrous methanol. The dropping funnel was adapted so that the methanol was added below the surface of the solution. The solution in the flask was heated to reflux and the addition of methanol was started. After approximately 30-40% of the methanol was added, the liquid in the azeotrope trap started forming two layers. The rate of methanol addition was adjusted so that the pot temperature did not fall below 105° C. The bottom layer in the azeotrope tape was continuously removed without allowing any to return to the reaction mixture. This solution contained methanol, HCl, H$_2$O and a small amount of toluene. The upper layer in the trap was mostly toluene with a small amount of methanol. When the layers in the azeotrope trap became one phase, the toluene reflux to the trap was continuously removed while the balance of the 200% excess methanol was added. At the end of the addition, the reaction mixture was cooled to less than 25° C. and analyzed by titration for parts per million unreacted Si—Cl. Based on the titration value, the reaction mixture was neutralized with a 50% solution of triethylamine in methanol. The solvent was then removed by distillation, preferably using vacuum to prevent the temperature from rising above 90° C. The residue obtained was cooled to room temperature and filtered through Celite 545, a diatomaceous earth. The yield was 680 grams (77%). Results from preparation of other bis(3-trimethoxysilylpropyl) diesters are shown in Table 1.

Examples 2 through 17 were carried out in the same manner as Example 1. The results of these Examples and the process conditions are set in Table 1.

TABLE 1

RESULTS FROM METHOXYLATION OF BIS-(3-TRICHLOROSILYLPROPYL)DIESTERS

| Experiment Number | Starting Allyl Esters | Solvent | % Solvent in Reaction | % Excess Methanol Used[2] | °C. Lowest Reflux Temperature During MeOH Addition | ppm ≡SiCl Before Neutralization | ppm ≡SiCl After Neutralization | % Yield | G.C. % Compound[3] 1 | G.C. % Compound 2 (product) | Neutralization Method |
|---|---|---|---|---|---|---|---|---|---|---|---|
| 2 | Diallyl maleate | Toluene | 60 | 250 | 66 | 804 | <20 | 74 | 34.3 | 18.7 | NaOMe |
| 3 | Diallyl maleate | Toluene | 60 | 250 | 69 | 178 | 72 | 75 | 41 | 17.5 | NaOMe |
| 4 | Diallyl maleate | Toluene | 60 | 148 | 71 | 200 | 23 | 80 | 31 | 26 | NaOMe |
| 5 | Diallyl maleate | Toluene | 75 | 176 | 80 | 167 | 95 | 72 | 36 | 31 | NaOMe |
| 6 | Diallyl maleate | Toluene | 60 | 50 | 104 | 1200 | 27 | 81 | 6.7 | 71 | NaOMe |
| 7 | Diallyl maleate | Toluene | 60 | 100 | 107 | 1878 | <20 | 68 | 3.6 | 72 | NaOMe |
| 8 | Diallyl maleate | Toluene | 60 | 100 | 105 | 686 | 40 | 83 | 2.8 | 77 | NaOMe |
| 9 | Diallyl maleate | Toluene | 60 | 168 | 108 | 1941 | <20 | 77 | 1.6 | 84 | Et$_3$N |
| 10 | Diallyl maleate | 50:50 toluene + Heptane | 57.3 | 200 | 101 | 340 | 23 | 81 | 1.6 | 79 | Et$_3$N |
| 11 | Diallyl maleate | Heptane | 54.3 | 150 | 98 | 2100 | 107 | 80 | 1.9 | 79 | Et$_3$N |
| 12 | Diallyl maleate | Heptane | 54.3 | 200 | 91 | 910 | <20 | 81 | 1.7 | 78 | Et$_3$N |
| 13 | Diallyl maleate[1] | Toluene | 47.2 | 200 | 105 | 1778 | <20 | 63 | 4.2 | 70 | Et$_3$N |
| 14 | Diallyl fumarate | Hexane | 82.1 | 200 | 58 | 167 | <20 | 81 | 4.3 | 88 | NaOMe |
| 15 | Diallyl succinate | Hexane | 82.1 | 100 | 59 | 2500 | <20 | — | 5.6 | 85 | NaOMe |
| 16 | Diallyl phthalate | Toluene | 62.6 | 100 | 104 | 1222 | <20 | 84 | — | — | Et$_3$N |
| 17 | Diallyl iso-phthalate | Toluene | 69.1 | 150 | 105 | 1997 | <20 | 80 | — | — | Et$_3$N |

[1]In this example, 2 moles of methylhydrogendichlorosilane were reacted and the tetramethoxy - derivative was obtained.
[2]Excess methanol is that amount added in excess of the stoichiometrically required amount.
[3]Compound 1 results from cleavage of one ester group by methanol to form the methyl ester.

I claim:
1. A process for producing silyl maleates comprising
(a) reacting a maleate of the formula,

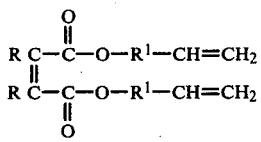

with

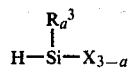

in the presence of a platinum catalyst and (b) reacting the intermediate product with an aliphatic alcohol of the formula $R^2OH$ where said intermediate product is present in an organic solvent and where said aliphatic alcohol is added to said intermediate product slowly over a period of at least six hours wherein said intermediate product is maintained at the reflux temperature of said organic solvent during said addition wherein the aliphatic alcohol is added to said intermediate product below and into the liquid layer of said intermediate product in the reaction vessel and wherein the reaction is carried out at the reflux temperature of said organic solvent and wherein there is continually removed overhead an azeotrope of alcohol, solvent and water in which is dissolved HCl so as to keep the concentration of the HCl and unreacted alcohol in the reaction mixture to a minimum to produce in at least 70% yield a silyl maleate of the formula,

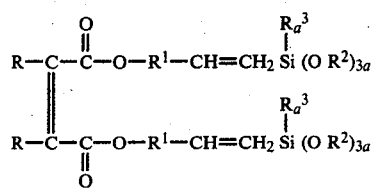

where $R^2$ and $R^3$ are monovalent hydrocarbon radicals of 1 to 8 carbon atoms, R is selected from hydrogen and monovalent hydrocarbon radicals of 1 to 8 carbon atoms, a varies from 1 to 2, X is halogen, and $R^1$ is a divalent hydrocarbon radical of 0 to 8 carbon atoms.

2. The process of claim 1 wherein in Step (a) after the reaction has initiated there is added an organic solvent and all of the chlorosilane by-product is distilled off.

3. The process of claim 1 wherein in Step (a) the organic solvent that is added is selected from the class consisting of aromatic solvents, aliphatic solvents, ethers, chlorinated and aliphatic solvents and methoxy ethers.

4. The process of claim 3 wherein the reaction in step (a) is carried out at a temperature varying from 25°-150° C. and wherein the hydride reactant is present at a concentration of 10-30% in excess.

5. The process of claim 4 where X is chlorine a is O, R is hydrogen, $R^2$ is methyl and wherein in step (a) all of the $SiCl_4$ that is formed as a by-product is stripped off before step (b) is carried out.

6. The process of claim 5 wherein the organic solvent in step (a) is toluene and the temperature of reaction is 80°-100° C.

7. The process of claim 1 wherein in step (b) there is added 50-300% of aliphatic alcohol in excess.

8. The process of claim 7 wherein the aliphatic alcohol is methanol.

9. The process of claim 7 wherein the organic solvent in (b) is selected from the class consisting of aliphatic solvents, aromatic solvents, chlorinated aliphatic solvents, chlorinated aromatic solvent, ether solvents and methoxy ether solvents.

10. The process of claim 9 wherein the aliphatic alcohol is added to said intermediate product over a period of 10 to 36 hours.

11. The process of claim 10 wherein after the concentration of chlorosilane reactant in step (b) has reached 10,000 parts per million or less there is added to the reaction mixture sufficient tertiary amine along with the aliphatic alcohol to complete the reaction, or a sufficient amount of the alkali metal salt of the aliphatic alcohol used.

12. The process of claim 11 wherein the tertiary amine is triethylamine or the alkali metal salt of the alcohol is sodium methoxide.

13. The process of claim 12 wherein the reaction product of step (b) has less than 50 parts per million of HCl.

14. The process of claim 13 wherein after step (b) is completed the organic solvent is distilled off and the amine salts or alkali metal halide salts are filtered out to result in the desired product.

15. The process of claim 14 wherein the organic solvent in step (b) is toluene, and the reaction is carried out at above 100° C.

16. A process for producing silyl fumarates comprising (a) reacting a fumarate of the formula,

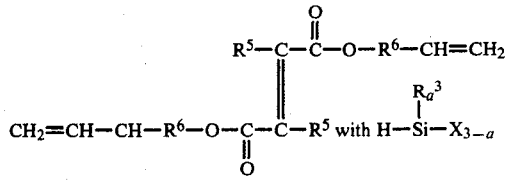

in the presence of a platinum catalyst and (b) reacting the intermediate product with an aliphatic alcohol of the formula $R^2OH$ where said intermediate product is present in an organic solvent and where said aliphatic alcohol is added to said intermediate product slowly over a period of at least six hours wherein said intermediate product is maintained at the reflux temperature of said organic solvent during said addition wherein the aliphatic alcohol is added to said intermediate product below and into the liquid layer of said intermediate product in the reaction vessel and wherein the reaction is carried out at the reflux temperature of said organic solvent and wherein there is continually removed overhead an azeotrope of alcohol, solvent and water in which is dissolved HCl so as to keep the concentration of the HCl and unreacted alcohol in the reaction mixture to a minimum to produce in at least 70% yield a silyl fumarate of the formula,

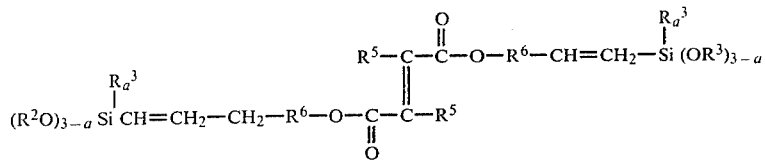

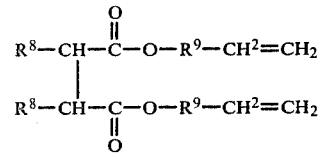

where $R^2$ and $R^3$ are monovalent hydrocarbon radicals of 1 to 8 carbon atoms, R is selected from hydrogen and monovalent hydrocarbon radicals of 1 to 8 carbon atoms, a varies from 1 to 2, X is halogen, and $R^6$ is a divalent hydrocarbon radical of 0 to 8 carbon atoms.

17. The process of claim 16 wherein in Step (a) after the reaction is preceded there is added an organic solvent and all of the chlorosilane byproduct is distilled off.

18. The process of claim 16 wherein in Step (a) the organic solvent is selected from the class consisting of aromatic solvents, aliphatic solvents, ethers, chlorinated aliphatic and aromatic solvents and methoxy ethers.

19. The process of claim 18 wherein the reaction in Step (a) is carried out at a temperature varying from 25°–150° C. and wherein the hydride reactant is present at a concentration of 10–30% in excess.

20. The process of claim 19 wherein X is chlorine, a is O, $R^5$ is hydrogen, $R^2$ is methyl and wherein in step (a) all of the $SiX_4$ that is formed as a by-product is stripped off before step (b) is carried out.

21. The process of claim 20 wherein the organic solvent in step (a) is toluene and the temperature of the reaction is 80° to 100° C.

22. The process of claim 16 wherein in step (b) there is added 50–300% of aliphatic alcohol in excess.

23. A process of claim 22 wherein the aliphatic alcohol is methanol.

24. The process of claim 22 wherein the organic solvent in step (b) is selected from the class consisting of aliphatic solvents, aromatic solvents, chlorinated aliphatic solvents, chlorinated aliphatic solvents, chlorinated aromatic solvents, ether solvents and methoxy ether solvents.

25. The process of claim 24 wherein the aliphatic alcohol is added to said intermediate product over a period of 10 to 36 hours.

26. The process of claim 25 wherein where the concentration of chlorosilane reactant in step (b) has reached 10,000 parts per million or less there is added to the reaction mixture sufficient tertiary amine along with the aliphatic alcohol stoichiometrically necessary to complete the reaction, or the stoichiometrically required amount of an alkali metalt salt of the alcohol used.

27. The process of claim 26 wherein the tertiary amine is triethylamine or the alkali metal salt of the alcohol is sodium methoxide.

28. The process of claim 27 wherein in the reaction product of Step (b) there is present less than 50 parts per million of HCl.

29. The process of claim 28 wherein after step (b) is completed the organic solvent is distilled off and the amine salts are filtered out to result in the desired product.

30. The process of claim 29 wherein the organic solvent in step (b) is toluene, and wherein the reaction is carried out at a temperature above 100° C.

31. A process for producing silyl succinates comprising (a) reacting a succinate of the formula, $$R^8-CH-\underset{\underset{O}{\|}}{C}-O-R^9-CH^2=CH_2$$
$$R^8-CH-\underset{\underset{O}{\|}}{C}-O-R^9-CH^2=CH_2$$

with $H-Si-X_{3-a}$ in the presence of a platinum catalyst and (b) reacting the intermediate product with an aliphatic alcohol of the formula $R^2OH$ where said intermediate product is present in an organic solvent and where said aliphatic alcohol is added to said intermediate product slowly over a period of at least six hours wherein said intermediate product is maintained at the reflux temperature of said organic solvent during said addition wherein the aliphatic alcohol is added to said intermediate product below and into the liquid layer of said intermediate product in the reaction vessel and wherein the reaction is carried out at the reflux temperature of said organic solvent and wherein there is continually removed overhead an azeotrope of alcohol, solvent and water in which is dissolved HCl so as to keep the concentration of the HCl and unreacted alcohol in the reaction mixture to a minimum to produce in at least 70% yield a silyl succinate of the formula,

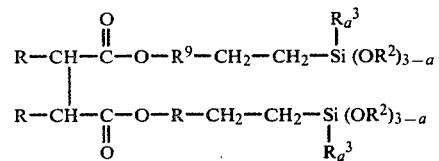

where $R^2$ and $R^3$ are monovalent hydrocarbon radicals of 1 to 8 carbon atoms, $R^8$ is selected from hydrogen and monovalent hydrocarbon radicals of 1 to 8 carbon atoms, a varies from 1 to 2, X is halogen, and $R^9$ is a divalent hydrocarbon radical of 0 to 8 carbon atoms.

32. The process of claim 31 wherein in Step (a) after the reaction is preceded there is added an organic solvent and all of the chlorosilane byproduct is distilled off.

33. The process of claim 31 wherein in Step (a) the organic solvent is selected from the class consisting of aromatic solvents, aliphatic solvents, ethers and chlorinated aliphatic and aromatic solvents and methoxy ethers.

34. The process of claim 33 wherein the reaction in step (a) is carried out at a temperature varying from 25°–150° C. and wherein the hydride reactant is present at a concentration of 10–30% in excess.

35. The process of claim 34 wherein X is chlorine, a is O, $R^8$ is hydrogen, $R^2$ is methyl and wherein step (a) all of the $SiCl_4$ that is formed as a byproduct is stripped off before step (b) is carried out.

36. The process of claim 35 wherein the organic solvent in step (a) is toluene and the temperature of the reaction is 80° to 100° C.

37. The process of claim 31 wherein in step (b) there is added 50% to 300% of aliphatic alcohol in excess.

38. The process of claim 37 wherein the aliphatic alcohol is methanol.

39. The process of claim 37 wherein the organic solvent in step (b) is selected from the class consisting of aliphatic solvent, aromatic solvents, chlorinated aliphatic solvents, chlorinated aromatic solvents, ether solvents, and methoxy ether solvents.

40. The process of claim 38 wherein the aliphatic alcohol is added to said intermediate product over a period of 10 to 36 hours.

41. The process of claim 40 wherein after the concentration of chlorosilane reactant in step (b) has reached 10,000 parts per million or less there is added to the reaction mixture sufficient tertiary amine along with the aliphatic alcohol, or the alkali metal salt of the alcohol to complete the reaction.

42. The process of claim 41 wherein the tertiary amine is triethylamine.

43. The process of claim 41 wherein the alkali metal salt of the alcohol is sodium methoxide.

44. The process of claim 43 wherein the reaction product of step (b) has less than 50 parts per million of HCl after the tertiary amine has been added to the reaction mixture.

45. The process of claim 44 wherein the reaction product of Step (b) has less than 50 parts per million of HCl after the alkali metal salt of the alcohol has been added to the reactional mixture.

46. The process of claim 44 wherein after step (b) is completed the organic solvent is distilled off and the amine salts are filtered out to result in the desired product.

47. The process of claim 45 wherein after step (b) is completed the organic solvent is distilled off and the alkali metal halide salts are filtered out to result in the distilled product.

48. The process of claim 46 wherein the organic solvent in step (b) is toluene, and wherein the reaction is carried out a temperature above 100° C.

49. A process for producing silyl phthalates comprising (a) reacting a phthlate of the formula,

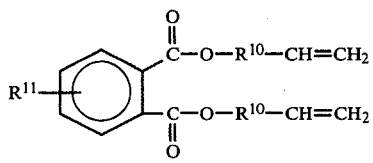

with H-Si-X$_{3-a}$ in the presence of a platinum catalyst and (b) reacting the intermediate product with an aliphatic alcohol of the formula R$^2$OH where said intermediate product is present in an organic solvent and where said aliphatic alcohol is added to said intermediate product slowly over a period of at least six hours wherein said intermediate product is maintained at the reflux temperature of said organic solvent during said addition wherein the aliphatic alcohol is added to said intermediate product below and into the liquid layer of said intermediate product in the reaction vessel and wherein the reaction is carried out at the reflux temperature of said organic solvent and wherein there is continually removed overhead an azeotrope of alcohol, solvent and water in which is dissolved HCl so as to keep the concentration of the HCl and unreacted alcohol in the reaction mixture to a minimum to produce in at least 70% yield a silyl phthlate of the formula,

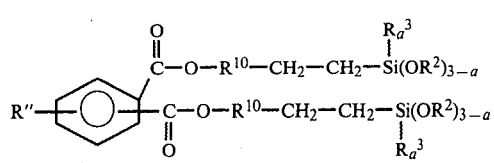

where R$^2$ and R$^3$ are monovalent hydrocarbon radicals of 1 to 8 carbon atoms, R$^{11}$ is selected from halogen, nitro or hydrogen, a varies from 0 to 2, X is halogen, and R$^{10}$ is a divalent hydrocarbon radical of 0 to 8 carbon atoms.

50. The process of claim 49 where X is chlorine, a is 0, R$^{11}$ is hydrogen, R$^2$ is methyl, and wherein step (a) all of the SiCl$_4$ that is formed as a byproduct is stripped off before step (b) is carried out.

51. The process of claim 50 wherein the organic solvent in step (a) is toluene and the temperature of the reaction is 80° to 100° C.

52. The process of claim 46 wherein in step (b) there is added 50 to 300% of aliphatic alcohol in excess.

53. The process of claim 50 wherein the aliphatic alcohol is methanol.

54. The process of claim 52 wherein the organic solvent in step (b) is selected from the class consisting of aliphatic solvent, aromatic solvents, chlorinated aliphatic solvents, chlorinated aromatic solvents, ether solvents, and methoxy ether solvents.

55. The process of claim 54 wherein the aliphatic alcohol is added to said intermediate product over a period of 10 to 36 hours.

56. The process of claim 55 wherein after the concentration of chlorosilane reactant in step (b) has reached 10,000 parts per million or less there is added to the reaction mixture sufficient tertiary amine along with the aliphatic alcohol to complete the reaction, or a sufficient amount of the alkali metal salt of the alcohol used.

57. The process of claim 56 wherein the tertiary amine is triethylamine, or the alkali metal salt of the alcohol is sodium methoxide.

58. The process of claim 57 wherein the reaction product of the step (b) has less than 50 parts per million of HCl after the tertiary amine or the alkali metal salt of the alcohol has been added to the reaction mixture.

59. The process of claim 58 wherein after step (b) is completed the organic solvent is distilled off and the amine salts or alkali metal halide salts are filtered out to result in the desired product.

60. The process of claim 59 wherein the organic solvent in step (b) is toluene, and wherein the reaction is carried out at a temperature above 100° C.

61. The process of claim 46 wherein step (a) after the reaction preceded there is added an organic solvent and all of the chlorosilane by-product is distilled off.

62. The process of claim 46 wherein Step (a) the organic solvent is selected from the class consisting of aromatic solvent, aliphatic solvents, ethers, and chlorinated aliphatic and aromatic solvents and methoxy ethers.

63. The process of claim 48 wherein the reaction in step (a) is carried out at a temperature varying from 25°-150° C. and wherein the hydride reactant is present at a concentration of 10-30% in excess.

* * * * *